US005797952A

United States Patent [19]
Klein

[11] Patent Number: 5,797,952
[45] Date of Patent: Aug. 25, 1998

[54] SYSTEM AND METHOD FOR DELIVERING HELICAL STENTS

[75] Inventor: Enrique J. Klein, Los Altos, Calif.

[73] Assignee: Localmed, Inc., Palo Alto, Calif.

[21] Appl. No.: 667,576

[22] Filed: Jun. 21, 1996

[51] Int. Cl.$^6$ .................................................. A61M 29/00
[52] U.S. Cl. ................................... 606/198; 623/1; 623/12
[58] Field of Search ........................... 606/1, 108, 191, 606/192, 194, 195, 198, 200, 104; 128/898, 899; 623/1, 12

[56] References Cited

U.S. PATENT DOCUMENTS

| | | |
|---|---|---|
| 4,665,918 | 5/1987 | Garza et al. |
| 4,723,549 | 2/1988 | Wholey et al. |
| 4,732,152 | 3/1988 | Wallsten et al. |
| 4,768,507 | 9/1988 | Fischell et al. |
| 4,795,458 | 1/1989 | Regan . |
| 4,848,343 | 7/1989 | Wallsten et al. |
| 4,875,480 | 10/1989 | Imbert . |
| 4,913,141 | 4/1990 | Hillstead . |
| 5,037,427 | 8/1991 | Harada et al. |
| 5,163,952 | 11/1992 | Froix . |
| 5,201,757 | 4/1993 | Heyn et al. |
| 5,246,445 | 9/1993 | Yachia et al. |
| 5,282,823 | 2/1994 | Schwartz et al. |
| 5,306,294 | 4/1994 | Winston et al. |
| 5,344,425 | 9/1994 | Sawyer . |
| 5,360,401 | 11/1994 | Turnland . |
| 5,372,600 | 12/1994 | Beyar et al. |
| 5,411,551 | 5/1995 | Winston et al. |
| 5,443,500 | 8/1995 | Sigwart . |
| 5,458,605 | 10/1995 | Klemm . |
| 5,458,615 | 10/1995 | Klemm et al. |
| 5,476,505 | 12/1995 | Limon . |
| 5,562,641 | 10/1996 | Flomenblit et al. .................. 606/198 |

FOREIGN PATENT DOCUMENTS

WO 94/16629 8/1994 WIPO.
WO 94/22379 10/1994 WIPO.

OTHER PUBLICATIONS

Beyar, Rafael et al. "Self–Expandable Nitinol Stent for Cardiovascular applications: Canine and Human Experience." (1994) *Catheterization and Cardiovascular Diagnosis* 32:162–170.

InStent® Cardiocoil™, Instent® of Eden Prairie, Minnesota (1995). –Product Brochure.

InStent®VascuCoil™ Self–expanding Vascular Stents . . . . InStent® of Eden Prairie, Minnesota (1995). –Product Brochure.

Scheneider Wallstent® Transhepatic Biliary Endoprosthesis with the Unistep™ Delivery System. Scheneider of Plymouth, Minnesota. –Product Bochure.

*Primary Examiner*—Michael Buiz
*Assistant Examiner*—William W. Lewis
*Attorney, Agent, or Firm*—Townsend and Townsend and Crew LLP

[57] ABSTRACT

A catheter for delivering self-expanding stents and other helical prostheses comprises a catheter body having a rotatable barrel at its distal end. The helical prosthesis is received within a helical channel on the rotatable barrel and covered with a retractable cover. Optionally, the channel includes a split membrane for covering the helical stent and preventing direct engagement by the stent against the cover. As the cover is retracted, the stent deploys radially outward and engages an inner wall of the lumen in which it is being deployed. Uncoiling or unwinding of the stent is accommodated by rotation of the barrel so that the stent is not dragged against the inner luminal wall potentially damaging said wall.

51 Claims, 6 Drawing Sheets

SYSTEM AND METHOD FOR DELIVERING HELICAL STENTS

BACKGROUND OF THE INVENTION

1. Field of the Invention

The present invention relates generally to medical devices and methods. More particularly, the present invention relates to apparatus and methods for delivering self-expanding helical prostheses within blood vessels and other body lumens.

In percutaneous transluminal coronary angioplasty (PTCA) procedures, a catheter having an expansible distal end, usually in the form of a balloon, is positioned in a lumen of a blood vessel with the distal end disposed within a stenotic atherosclerotic region of the vessel. The expansible end is then expanded to dilate the vessel and, upon withdrawal, restores adequate blood flow through the diseased region.

While angioplasty has gained wide acceptance, it continues to be limited by two major problems, abrupt closure and restenosis. Abrupt closure refers to the acute occlusion of a vessel immediately after or within the initial hours following the dilatation procedure. This complication occurs in approximately one of twenty cases and frequently results in myocardial infarction and death if blood flow is not quickly restored. Restenosis refers to the re-narrowing of an artery after an initially successful angioplasty. Occurring usually within the initial six months after angioplasty, and restenosis afflicts approximately one in three cases. That is, approximately one in three patients will require additional revascularization procedures.

Many different strategies have been tried with different degrees of success to reduce restenosis and abrupt closure, including pharmacologic (e.g., systemic and localized administration of anti-proliferative agents and other drugs) and mechanical (e.g., prolonged balloon inflations, atherectomy, laser angioplasty, post-angioplasty thermal conditioning, and stenting). Of particular interest to the present invention, the intravascular delivery and implantation of stents to a blood vessel following balloon angioplasty procedures has proven to be of great value. The first stent to achieve widespread acceptance is the Palmaz-Schatz stent available from Johnson & Johnson Interventional Systems, a division of Ethicon, Inc., Somerville, N.J. The Palmaz-Schatz stent is a slotted tube formed from a malleable material. For delivery to the target site, the stent is usually placed over the balloon of a balloon delivery catheter having a non-distensible balloon. The angioplasty balloon catheter is then exchanged with the delivery catheter, and the stent positioned at the angioplasty treatment site. The balloon of the delivery catheter is then inflated to expand the stent in situ in order to implant the stent within the blood vessel.

A second class of stents is commonly referred to as "self-expanding stents" or "resilient stents" (in contrast to malleable stents as discussed above). This class of stent is defined primarily by the materials from which the stent is fabricated as well as the method in which the stent is retained and deployed. The materials of self-expanding stents may be resilient (spring-like) so that the stent may be delivered in a radially constrained state and implanted by releasing the stent from the constraint, whereby the stent springs back to its larger diameter configuration. Alternatively, the stents may be formed from shape memory alloys where the stents are delivered in a reduced diameter configuration and subjected to conditions which cause a phase change which result in radial expansion of the stent structure within the blood vessel. Most commonly, such stents are formed from a nickel titanium alloy and are delivered in a deformed, smaller diameter configuration. Such stents are heated in situ to recover their original "memorized" larger diameter configuration. Typically, such alloys exhibit a crystallographic transformation from a martenistic structure at a lower temperature prior to delivery to an austensitic structure at a higher temperature to which they are subsequently exposed. In some cases, the stents are quickly heated to a temperature somewhat above body temperature when ready for deployment in the blood vessel lumen. In other cases, transformation to the austenitic phase will occur when the stent is exposed to body temperature.

Such self-expanding stents are available in a wide variety of geometric configurations, including slotted tubes or wire meshes which expand to form diamond-shaped grids, spirally wrapped sheets which unfurl as they expand, and the like. Of particular interest to the present invention, helical coil stents comprise a wire or ribbon element which is helically wound so that it resembles a coil spring. In the case of resilient materials, the helical stent may be reduced in diameter by "torquing it down" on a delivery catheter. The torqued stent is then radially constrained, typically by covering it with a tube or sheath. The tube or sheath may then be retracted, permitting the coil stent to resiliently expand into the blood vessel lumen. In the case of shape memory alloys, the coil will be deformed while in the martensitic phase onto the catheter and will retain its deformed, smaller diameter configuration until subjected to a higher temperature. After axially positioning the coil stent at a target location in the blood vessel, body temperature may be sufficient to effect phase change expansion or a heated fluid such as saline may be directed against the coil to cause it to rapidly expand. Alternatively, the coil may be actively cooled prior to introduction, and the cooling then terminated to permit it to heat to body temperature and self-deploy.

Helical coil stents have a number of significant advantages. In particular, they are highly flexible and can be delivered to even the most tortuous regions of the vasculature, i.e. they track better to the target site. Additionally, they are relatively easy and inexpensive to fabricate. Coil stents are also able to conform better to curved and irregular vessel geometries than many other types of stents. In particular, after deployment, coil stents are usually free from angular discontinuities at each end. Coil stents can further be deployed in the presence of arterial branches while reducing the likelihood that such branches will be occluded because of the smaller coverage ratio of coils (i.e., there is often a relatively wide spacing between adjacent coil). The space between adjacent coils can also provide access to perform procedures in side branches even after stent placement. Additionally, coil stents are well suited for "bailout" procedures where potentially occluding materials, such as intimal flaps may be present after angioplasty.

While enjoying the advantages set forth above, helical coil stents also suffer from disadvantages. Generally, as a result of their geometry, helical stents will elongate when they are radially compressed onto a delivery catheter. Thus, the stent will foreshorten as it is released. Such foreshortening renders placement of radiopaque stents under fluoroscopy very difficult. Additionally, the sudden expansion of a radially constrained stent can release significant energy within the blood vessel and in some instances may induce vascular spasm. While it is possible to release the stent gradually by slowly withdrawing a tubular cover, such deployment causes the free end of the stent which has been released to turn or unwind within the blood vessel as the coil diameter increases. Such movement can cause trauma to the arterial wall.

For these reasons, it would be desirable to provide improved systems and methods for delivering helical coil stents and prostheses to body lumens, such as blood vessels. In particular, it would be desirable to provide systems and methods which assure that the helical prosthesis is carried on a delivery catheter with a length equal to that of the fully deployed prosthesis. For example, it would be desirable to provide methods for loading helical prosthesis onto catheters so that the length of the prosthesis on the catheter is equal to that of the prosthesis when unconstrained and fully expanded. It would further be desirable to provide delivery catheters and methods which permit the progressive release of helical prostheses from the catheter without causing the prosthesis to unwind and rotate relative to the blood vessel wall. Moreover, it would be desirable to provide delivery catheters which permit a helical prosthesis to be at least partially radially constrained on a catheter within a helical groove while optionally being partially radially constrained or shielded by a tubular cover or sheath. The present invention is intended to address at least some of these concerns.

2. Description of the Background Art

U.S. Pat. No. 4,768,507, illustrates a catheter having a helical channel for receiving a self-expanding helical stent and a retractable cover for holding and selectively releasing the stent. U.S. Pat. No. 5,476,505, describes a catheter including coaxial shafts for delivering self-expanding helical stents. One end of the stent is held on one shaft and the other end of the stent is held on the other shaft. The shafts may be torqued and rotated relative to each other in order to load and release the stent. One type of self-expanding stent is commercially available from Schneider (USA) Inc., Pfizer Hospital Products Group, Plymouth, Minn. 55442, under the trademark WALLSTENT®. The WALLSTENT® stent comprises counterwound interwoven helical monofilament wire, and delivery systems for the stent are described in U.S. Pat. Nos. 4,732,152; 4,848,343; and 4,875,480, and in a product insert entitled "WALLSTENT® Transhepatic Biliary Endoprosthesis with the Unistep™ Delivery System" (undated). Another self-expanding helical coil stent is commercially available under the tradenames VascuCoil™ self-expanding vascular stent and CardioCoil™ self-expanding cardiovascular stent from InStent, Eden Prairie, Minn. 55346. The VascuCoil™ stent comprises a nickel titanium wire coil, as described in InStent product brochures entitled "VascuCoil™ Self-expanding Vascular Stents . . ." ©1995 InStent and "CardioCoil™ Self-expanding Cardiovascular Stent" ©1995 InStent. Delivery systems for the InStent® stents are described in U.S. Pat. Nos. 5,372,600; 5,246,445; WO 94/22379; and WO 94/16629. U.S. Pat. No. 5,246,445, describes a catheter for delivering intraurethral stents where the two ends of the stent are held on coaxial shafts so that relative rotation of the shafts can constrict and expand the stent. Use of the InStent® stents is described in Beyar et al. (1994) *Cath. Cardiovasc. Diag.* 32:162–170. Self-expanding helical coil stents which are composed of a shape memory alloy and delivered by heating in situ are described in U.S. Pat. Nos. 4,795,458 and 5,037,427. Catheter systems for delivering self-expanding stents are described in U.S. Pat. Nos. 4,655,918; 4,723,549; 5,201,757; 5,360,401; 5,458,605; and 5,458,615. Other self-expanding stents and delivery systems are described in U.S. Pat. Nos. 4,913,141; 5,163,952; 5,282,823; 5,306,294; 5,344,425; 5,411,551; and 5,443,500.

SUMMARY OF THE INVENTION

According to the present invention, devices, systems, and methods are provided for the delivery of self-expanding helical prostheses to target locations within body lumens. While particularly intended for the post-angioplasty delivery of intravascular stents, the method would also find use with the delivery of other stents, grafts, and the like, to other body lumens, such as the delivery of urethral stents for the treatment of prostate conditions, and the like. The self-expanding helical stent will comprise at least one elongate element, such as a wire, filament, ribbon, or the like, formed into a cylindrical helix, typically having a uniform diameter and uniform spacing between adjacent turns. The helical prosthesis may be formed of any resilient and/or shape memory alloy material of a type conventionally used in self-expanding medical implant devices. Preferably, the coil will be composed of a shape memory alloy of nickel and titanium, such as the commercially available alloy known as NITINOL®, which can act as both a shape memory alloy, i.e., when appropriately alloyed and fabricated it will respond to a temperature change to induce a phase change and reversion to a "memorized" expanded shape, or as a superelastic material which can be constrained and upon release will return to its original configuration in the absence of temperature and phase changes.

In addition to simple helical shapes, stents delivered by the catheter and method of the present invention may employ more complex geometries. For example, the stents may be in the form of serpentine or zig-zag elements which possess a secondary helical winding. See, e.g., U.S. Pat. No. 5,405,377 to Cragg, the full disclosure of which is incorporated herein by reference. Additionally, the basic helical structure can be augmented with axial, transverse, or other projections which help fill the gaps between adjacent turns of the helical coil as the stent is expanded. A variety of other specific stent configurations may also be employed.

It will be appreciated that such helical coil prostheses will have an unconstrained configuration at body temperature characterized by an unconstrained axial length, diameter, and number of helical turns. When constrained onto a delivery catheter, however, such helical coil prostheses will usually be axially elongated as a result of the reduction in diameter. Moreover, when released from constraint, or induced to expand by a temperature change, the ends of such helical coil prostheses will "unwind" relative to each other as the diameter increases and the number of helical turns decreases. Both the length change and the unwinding or uncoiling of the prosthesis are problematic during deployment of the prosthesis, and the present invention addresses both of these problems as described in detail below.

According to a first aspect of the present invention, a catheter for delivering the self-expanding helical prosthesis comprises a catheter body having a proximal end and a distal end, and a barrel rotatably attached to the distal end of the catheter body. The helical prosthesis is mounted on the barrel, and an axially retractable cover is disposed over the prosthesis and the barrel. As the cover is retracted, a first end of the helical coil prosthesis will be released and will deploy radially outwardly until it engages the inner luminal wall of the blood vessel or other body lumen. At that point, the free end of the helical prosthesis will at least partially anchor against the luminal wall. Further retraction of the cover will permit successive turns of the coil to be released. As the coil thus unwinds, the barrel on the catheter will be able to rotate relative to the catheter body to prevent the free end of the coil from being dragged against the luminal wall. In this way, mechanical trauma caused by the release of the coil is significantly reduced.

Preferably the barrel will have a helical channel formed thereover for receiving the helical prosthesis. More preferably, the helical channel will have a penetrable retaining structure for protecting and at least partially containing the helical prosthesis while the cover is being axially retracted. These aspects of the catheter design are discussed in more detail below.

The axially retractable cover may comprise any structure which can cover and optionally radially constrain the helical prosthesis on the catheter, usually within the helical channel. Typically, the cover will comprise a cylindrical sheath or sleeve which fully and continuously covers the helical channel and prosthesis. In the exemplary embodiment, the cylindrical sheath is sized only slightly longer than the helical prosthesis itself, and a pull cord or tube is provided to permit axial retraction from the proximal end of the catheter. Typically, the pull cord will extend through a lumen within the catheter body. Alternatively, the axially retractable cover could comprise a braid or mesh structure, a reinforced membrane, or virtually any other retaining structure which can be retracted in order to permit radial expansion of the helical prosthesis from the catheter body.

In a second aspect of the present invention, a catheter for delivering self-expanding helical prosthesis comprises a catheter body having a proximal end, a distal end, and a helical channel formed therein near the distal end. The helical channel receives the helical prosthesis and includes a penetrable (typically split) retaining structure formed thereover. The catheter further includes an axially retractable cover, generally as set forth above. The penetrable retaining structure is advantageous since it prevents direct contact between the helical prosthesis and the axially retractable cover, where such contact could frictionally interfere with retraction of the cover. It will be appreciated that a wide variety of other penetrable structures, such as fingers, detents, and the like could be provided to retain the helical prosthesis within the channel and prevent direct engagement of the prosthesis against the cover. The retaining structures by themselves, of course, will have insufficient mechanical strength to prevent self-expansion of the prosthesis therethrough i.e., once the cover is withdrawn, the stent will be able to expand outwardly through the retaining structure under its own radial expansion force. It is only when the cover is in place that the retaining structure(s) will hold the prosthesis within the channel.

In a third aspect of the present invention, a catheter system for delivering a helical prosthesis comprises the prosthesis and associated catheter. The helical prosthesis is a self-expanding helical element having when unconstrained at body temperature an axial length, a diameter, and a number of turns. The catheter comprises a catheter body having a proximal end, a distal end, and a helical channel formed near the distal end for receiving the prosthesis. The helical channel has a number of turns and spacing between adjacent turns which allow the helical prosthesis to be carried on the channel in a radially reduced diameter condition with a length equal to the unconstrained length of the prosthesis.

Preferably, the helical channel has adjacent turns which are substantially equally spaced-apart and wherein the spacing conforms to the formula:

$$p = P\,(d/D),$$

wherein p is the helical channel spacing on the catheter body, P is the spacing between adjacent turns on the unconstrained prosthesis, d is the diameter of the helical prosthesis on the catheter body, and D is the unconstrained diameter of the prosthesis. By configuring the helical channel to conform to this formula, the helical prosthesis will be held in a configuration which assures that its constrained length is equal to its unconstrained length after it is released from the catheter.

Typically, when disposed on the catheter, the helical prosthesis will have a length in the range from 10 mm to 60 mm, an outer diameter in the range from 2 mm to 4 mm, and a number of turns in the range from 5 to 70. When unconstrained and released from the catheter, the helical prosthesis will usually have a length in the range from 10 mm to 60 mm, which length will typically be equal to that in the constrained configuration, an outer diameter in the range from 2.5 mm to 12 mm, and a number of turns in the range from 4 to 25.

The helical prosthesis may also include an anchor formed at at least one end. Such anchor will be configured to be received in and mate with a receptacle formed at a corresponding end of the helical channel in the catheter body. Preferably, such anchors and receptacles will be formed at both ends of the helical prosthesis and helical channel, respectively. More preferably, the anchor will be a flat loop, disk, or other similar structure which will lie flat (or flared slightly outwardly) against the luminal wall when the helical prosthesis is fully expanded. The use of such anchors and receptacles further assures that the length of the helical prosthesis is precisely maintained at the unconstrained length when the prosthesis is constrained and held on the delivery catheter.

The present invention still further provides methods for loading a helical prosthesis on a catheter. Such methods comprise radially constraining or loading a self-expanding helical prosthesis having when unconstrained at body temperature an axial length, a diameter, and a number of turns. When constrained over the delivery catheter, the prosthesis is wound or torqued in order to increase the number of turns relative to the number of turns in the unconstrained configuration. By properly choosing the number of turns, typically in accordance with the formula above, the constrained and unconstrained axial lengths can be maintained precisely equal. Usually, the constraining step in this method comprises capturing the helical prosthesis within a cover which is axially retractably mounted on the catheter. The constraining step may further comprise capturing the helical prosthesis within a helical channel on the catheter, where the channel has a diameter and pitch which can be calculated by the above formula.

The present invention further provides a method for deploying a self-expanding helical stent. The method comprises providing a catheter having a self-expanding helical prosthesis rotatably mounted thereon. The prosthesis is initially carried in a radially collapsed configuration, and the catheter manipulated to position the prosthesis at a target site within the blood vessel or other body lumen. The prosthesis is progressively released so that successive turns of the prosthesis engage the wall of the body lumen. A distal portion of the catheter which carries the prosthesis is able to rotate so that unwinding and uncoiling of the prosthesis does not cause the prosthesis to rotate relative to the luminal wall, thus reducing risk of trauma and damage to the wall.

DESCRIPTION OF THE SPECIFIC EMBODIMENTS

Figure 1:
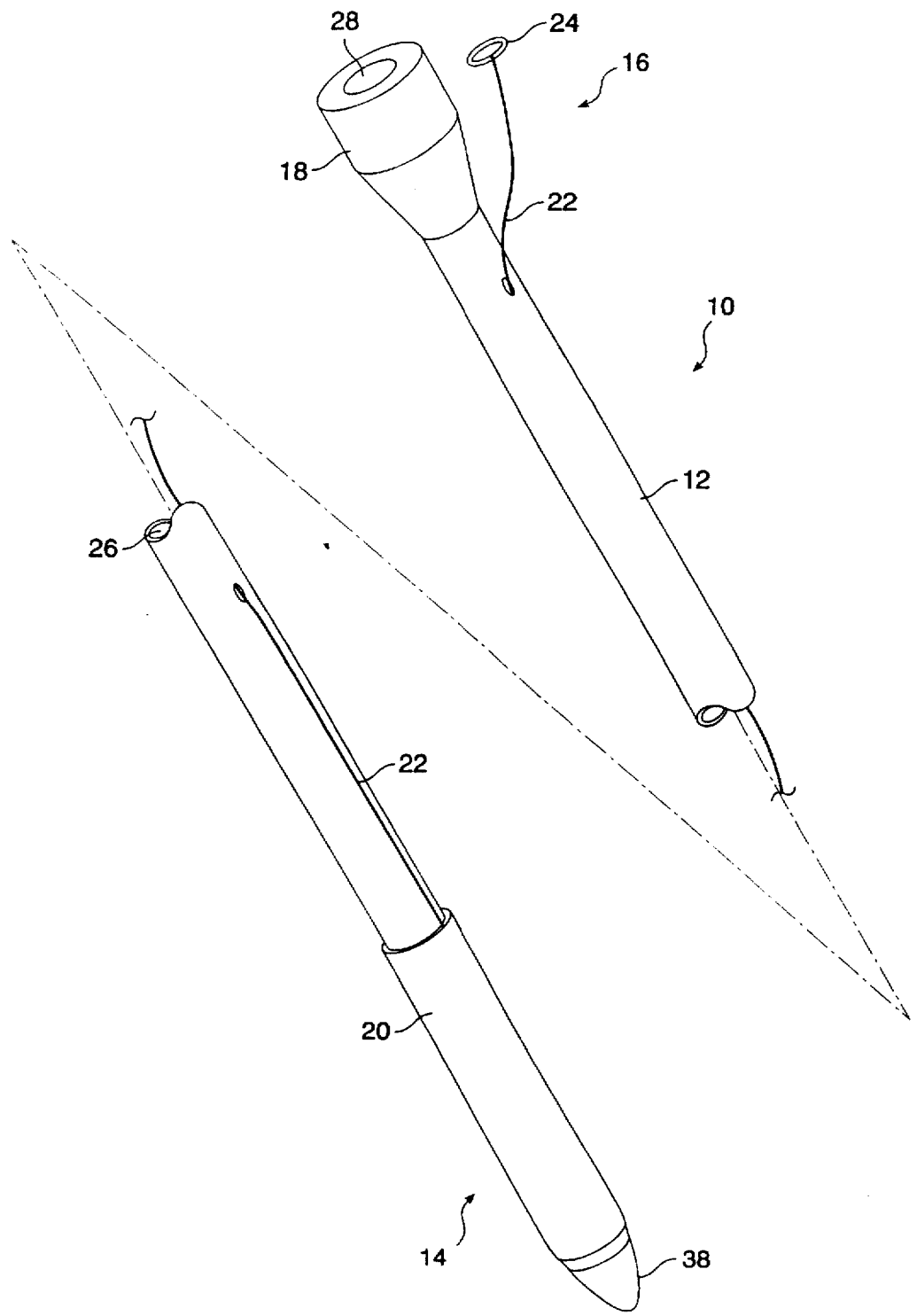
FIG. 1 is a perspective view of a helical prosthesis delivery catheter constructed in accordance with the principles of the present invention.

The present invention provides methods, systems, and devices for the intraluminal delivery of self-expanding helical prostheses. By "intraluminal," it is meant that the delivery occurs at a target site within a body lumen, usually being within the patient vasculature, more usually being within the arterial system, including the coronary arteries, the peripheral arteries, and the cerebral arteries. The methods and devices of the present invention, however, are not limited to use in the vascular system, and may also be advantageously employed in other body structures, including the prostate via the prostatic urethra, (e.g., to treat benign prostatic hypertrophy (BPH), or adenocarcinoma), the fallopian tube via its lumen (to treat strictures), brain parenchyma (to treat Parkinson's disease), and the like.

The "target site" within the body lumen will usually be diseased or be suspected of being diseased. In the case of vascular treatment, the target locations will usually be stenotic regions which have previously been treated by conventional balloon angioplasty procedures using a balloon angioplasty catheter or other primary treatment procedures, such as atherectomy, laser angioplasty, ultrasonic ablation, or the like.

The apparatus and methods of the present invention are intended for the delivery of self-expanding helical prostheses to the target site in the body lumen. Such prostheses include both stents and graft structures, particularly intravascular stents and grafts of the type used to maintain vessel patency following balloon angioplasty and other primary treatment procedures. The helical prostheses may be formed from elongate elements such as wires, filaments, ribbons, and the like, or may be machined from hypodermic or other small tubing, preferably by laser milling techniques. The resulting stents will be formed into helices having physical characteristics which permit the helices to be initially maintained in a narrow diameter configuration and thereafter released or otherwise caused to assume a radially expanded configuration. The helical prostheses will thus be composed of materials which permit such size transitions, typically being either resilient (springy) metals, such as certain stainless steels or special alloys having superelastic properties. Preferably, the materials will be superelastic alloys which have been treated to display superelastic behavior in a temperature range from below room temperature, i.e. 20° C., to above body temperature, i.e. 37° C. The most notable of such alloys is nickel titanium alloy, known commonly as NITINOL®. Superelasticity means that the alloys can be significantly deformed with up to an 8% strain, (e.g., the coils of the present invention can be significantly radially constricted) but will fully return to their preconstrained configuration without permanent deformation after the constraint is released. Alternatively, NITINOL® can also be fabricated so that it will undergo a crystallographic transformation from its martensitic phase in which it is malleable to its austenitic phase in which it is resilient or superelastic, at a predetermined temperature, e.g. 32° C., which is slightly below body temperature but above body temperature. The coil remains martensitic below the transition temperature, but becomes austenitic and expands above the transition temperature, e.g., at body temperature of 37° C. Such "shape memory" expansion to a desired expanded diameter can be imparted by thermal conditioning of the stent according to well known principles. The formation of coil stents from NITINOL® alloys having both superelastic and shape memory properties are well described in the patent, scientific, and medical literature. See, for example, U.S. Pat. Nos. 4,795,458 and 5,037,427, and PCT publication WO 94/16629.

Catheters according to the present invention will comprise a catheter body having a proximal end and a distal end, and dimensions suitable for delivery to the intended intraluminal target site. For intravascular uses, the catheter body will typically have a length in the range from about 50 cm to 250 cm, usually from about 100 cm to 175 cm. The catheter body will have an outside diameter in the range from 1 French (1 Fr=0.33 mm) to 12 French, typically from 2 Fr to 11 Fr, more usually from 3 Fr to 10 Fr. The catheter body will usually include at least a single lumen for introduction over a conventional guidewire, and may also include other lumens for other purposes, such as delivery of a heated fluid to induce expansion of helical prostheses composed of shape memory alloys. The guidewire lumen may extend for the full length of the catheter body, for over-the-wire deployment, or may extend only partly through the distal end of the catheter body, for rapid exchange deployment. The catheter body will be formed from conventional materials, typically by extrusion of polymeric materials, such as polyethylenes, including polyethyleneterephthalate, polyamides, polyesters, polyurethanes, polyvinylchlorides, and the like.

Referring now to FIG. 1, a catheter system 10 comprising a helical prosthesis delivery catheter 12 constructed in accordance with the principles of the present invention will be described. The delivery catheter 12 comprises a catheter body having a distal end 14 and a proximal end 16 and a proximal housing 18 attached to the proximal end of the catheter body. An axially retractable cover 20 is slidably disposed near the distal end 14 of the catheter 12 and covers the helical prosthesis, as described below. The cover 20 has a relatively short length, typically in the range from 15 mm to 65 mm, and is usually just sufficient to cover the underlying helical prosthesis. A pull cord 22 is provided for axially retracting the cover in the proximal direction. The pull cord 22 extends on the outside of the catheter body for a distance sufficient to permit full retraction of the cover, and then will usually pass into a lumen within the catheter body. Alternatively, the pull cord 22 which is shown as being exposed on the outer surface of the catheter body of catheter 12 in FIG. 1 may be recessed within a channel which is covered by a split or scored membrane or other structure which permits the cord to be axially retracted therethrough. Covering or enclosing the pull cord is often preferred to provide improved guidance for the pullwire and to minimize the risk of injury to the blood vessel wall as the catheter is introduced or withdrawn. Conveniently, a ring 24 or other structure will be included at the end of the pull cord 22 to facilitate its axial retraction. Optionally, the ring may exit through a side arm (not shown) on hub 18. The catheter body of catheter 12 will usually include at least one additional lumen 26 extending at least partially therethrough for receiving a conventional guidewire. As illustrated in FIG. 1, the lumen 26 extends the full length from the distal end 14 to the proximal end 16 and passes out through port 28 in the housing 18.

The axial cover 20 is shown to be a cylindrical sheath in FIG. 1. As discussed above, a variety of other cover structures could also be employed, where the primary requirement is that the structure be axially retractable or otherwise movable so that the helical prosthesis thereunder can be fully exposed to permit self-expansion and deployment. The use of the cylindrical structure, however, is particularly convenient since it is easy to fabricate and readily deployed by the physician user.

As an alternative to the pull cord 22, the cover 20 could extend fully to the proximal end of the catheter 12, i.e. the cover could be formed as a sleeve which extends fully over the length of the catheter but which terminates just distal to the proximal portion of the catheter body. A variety of other specific designs would also be possible, with the primary requirement being the ability to retract the cover from the proximal end of the catheter.

Figure 2:
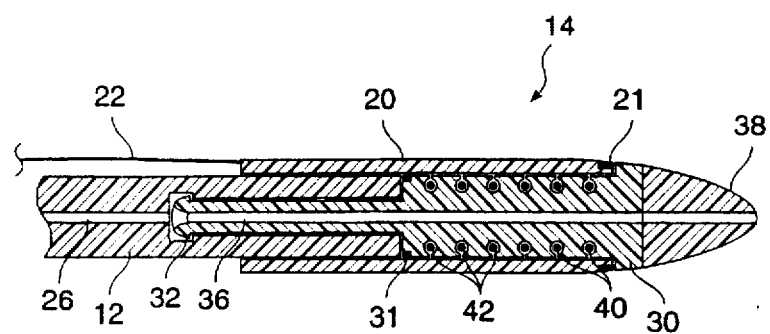
FIG. 2 is an enlarged view of the distal end of the catheter of FIG. 1, shown in section.

Referring now to FIG. 2, the distal end 14 of the catheter 12 is shown in cross-section. The catheter body of catheter 12 terminates in a rotatable barrel 30 which has a tapered connector 32 at its proximal end and a soft tip 38 at its distal end. The connector 32 is received in an interior cavity 34 of the catheter body, and the rotatable barrel has a lumen 36 which is coaxial with the lumen 26 of the catheter body. A helical prosthesis 40 is received within helical channels 42 formed on the exterior surface of the rotatable barrel 30. As the cover 20 is axially retracted, the adjacent turns of the helical channel 42 will be gradually exposed in a direction from distal to proximal. As described in more detail below, such exposure of the helical channel 42 will permit the self-expanding helical prosthesis therein to emerge from the channel by unwinding or uncoiling and expanding radially outward. At first, the free end of the prosthesis 40 will expand and assume a larger diameter as it emerges from the barrel 30. The free end will eventually reach and engage the lumenal wall, pushing the barrel 30 in the opposite direction generally against an opposed portion of the lumenal wall. Initially, the barrel 30 will not rotate. As soon as the free end of the prosthesis 40 engages and anchors against a luminal wall, however, the expansion and unwinding of the prosthesis is accommodated by rotation of the barrel. That is, the barrel will rotate in a direction to accommodate the unwinding and uncoiling of the prosthesis. If the prosthesis were fixed to the catheter during the deployment in a manner which did not permit such rotation, the free end of the prosthesis would be forced to rotate against the luminal wall, potentially causing injury.

Figure 6A:
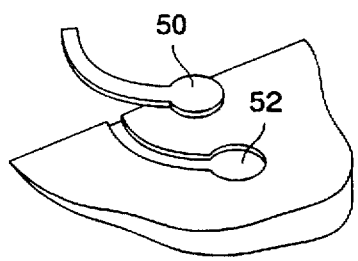
FIGS. 6A and 6B are detailed views of the end anchors of the helical prostheses of the present invention.

Radiopaque markers will be provided on the catheter and stent as necessary to enable fluoroscopic visualization. In the case of NITINOL® and other inherently radiopaque materials, it will usually not be necessary to provide for additional radiopaque markings on the stent itself. In the case of stainless stain stents, and other less radiopaque materials, it will usually be desirable to provide additional radiopaque markings, at least at the proximal and distal ends of the stent. For example, portions of the helical coil of the stent and/or the proximal or distal anchors (as described in more detail with reference to FIGS. 6A and 6B), could be plated with a radiopaque material, such as gold or platinum. Alternatively, the radiopaque materials could be otherwise attached to the coil or other portions of the stent. In addition to the stent, it will usually be desirable to provide radiopaque markers on the catheter. In particular, at least one marker 21 (FIG. 2) should be provided near the distal end of the cover 20 so that full retraction of the cover past the stent can be confirmed. It will usually be desirable to provide at least a second radiopaque marker 31 (FIG. 2) at or near the proximal end of the rotating barrel 30. The presence of the proximal marker 31 on the barrel allows the physician to further confirm that the cover 20 has been fully retracted by noting the passage or proximity of the distal marker 21 on the cover over the proximal marker 31 on the barrel.

Figure 3A:
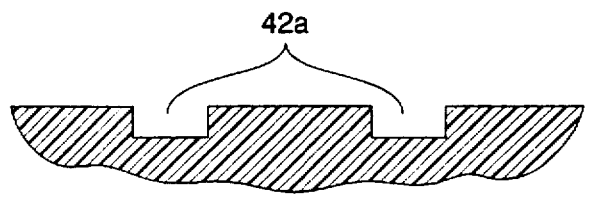
FIGS. 3A–3C are detailed, alternative views of the prosthesis-retaining channels formed in the catheter of FIG. 2.
Figure 3B:
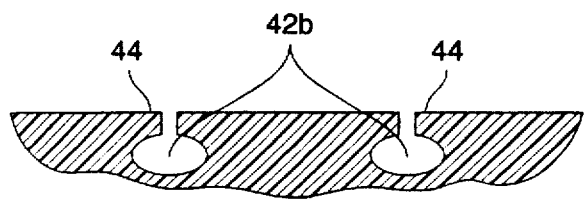
Figure 3C:
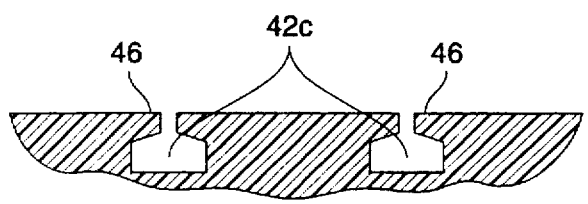

Referring now to FIGS. 3A–3C, a variety of cross-sections for the helical channel 42 are possible. In FIG. 3A, channel 42a has a simple, rectangular cross-section. With such cross-section, prosthesis held therein will be disposed in frictional apposition to the interior surface of the cover 20 as the cover is retracted. Such friction can interfere with the retraction of the cover. An alternative channel configuration 42b is shown in FIG. 3B. There, a split membrane 44 is formed over the channel 42b. The membrane retains the prosthesis therein and does not allow the prosthesis to engage against the interior surface of cover 20. As soon as the cover is retracted, however, the membrane can open and permit release of the prosthesis. A third alternative luminal cross-section 42c is illustrated in FIG. 3C. The cross-section 42 also includes a split membrane 46 but has a pentagonal cross-section, rather than generally circular or oblong as shown in FIG. 3B.

Figure 4A:
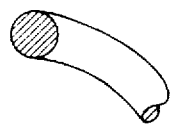
FIGS. 4A–4D illustrate alternative cross-sections of the elongate elements which may be used to form the helical prostheses of the present invention.
Figure 4B:
Figure 4C:
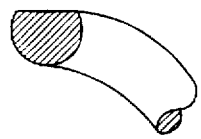
Figure 4D:

The helical prosthesis will generally be formed from a wire monofilament or ribbon, as described above. The wire will usually be circular, as shown in FIG. 4A but can have a variety of other cross-sections, as shown in FIGS. 4B–4D.

Figure 5:
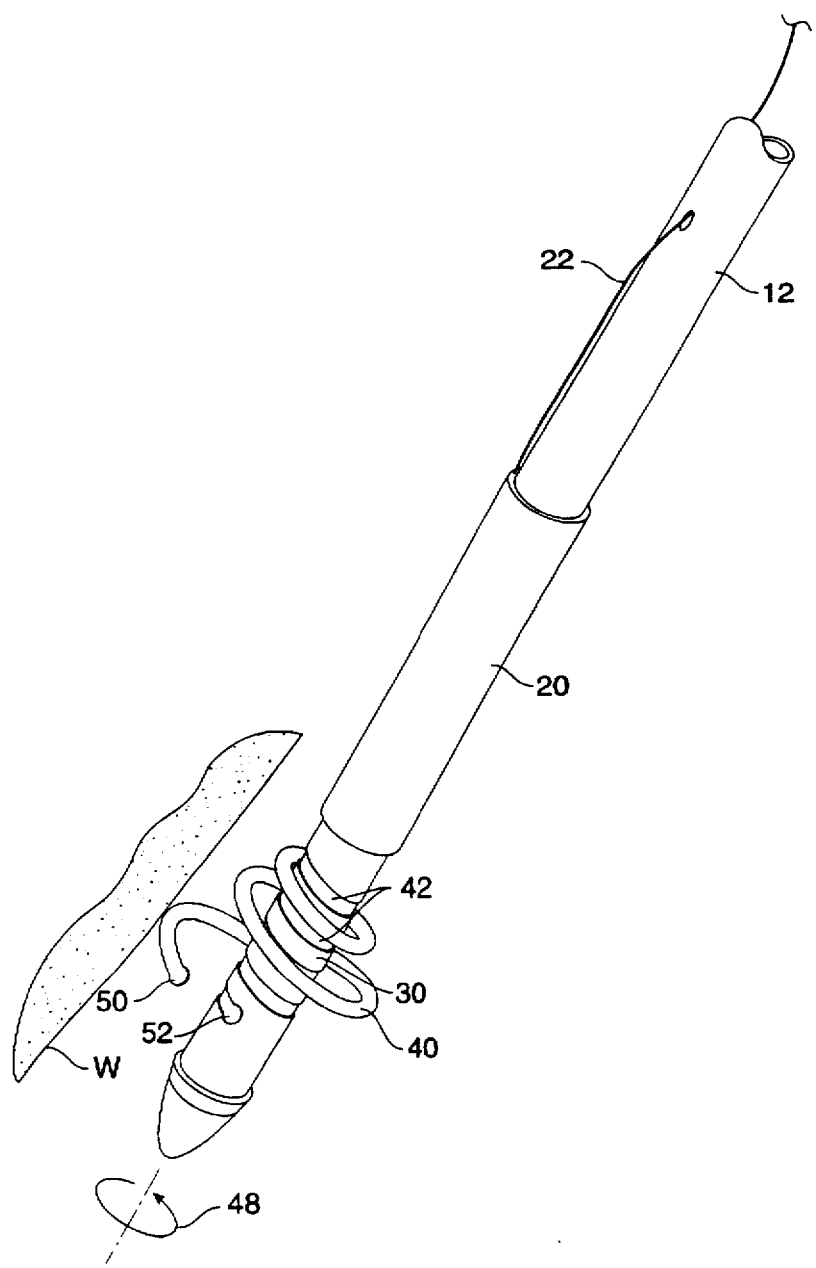
FIG. 5 is an enlarged view of the distal end of the catheter of FIG. 1, shown with the prosthesis cover partially retracted and the helical prosthesis partially expanded.

Referring now to FIG. 5, release of the helical prosthesis 40 from the delivery catheter 12 is illustrated. As the cover 20 is axially retracted in the proximal direction by pull wire 22, a free end 50 (having an anchor formed at its end as described below) is released and extends radially outwardly until it engages the inner lumen or wall W. Initially, expansion of the prosthesis coil will press the catheter body against an opposed portion of the blood vessel wall. As the stent further uncoils, the distal end of the catheter will undergo some precession about the center of the blood vessel lumen. The helical prosthesis 40 unwinds and enlarges over successive turns as illustrated. During such release and unwinding, the barrel 30 rotates about the axis in the direction shown by arrow 48.

Figure 6B:
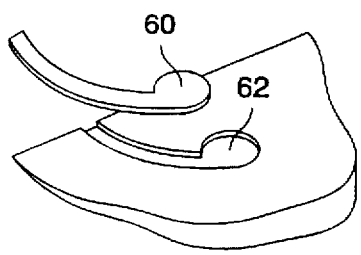

In a preferred aspect of the design of catheter 12, a receptacle 52 is formed in the outer surface of the barrel 30 at one end of the helical channel 42. Receptacle 52 conforms to and mates with the anchor 50 at the corresponding end of the helical prosthesis 30. In this preferred design, the anchor 50 is a flat disk. Preferably, a corresponding anchor and receptacle are formed at the other (proximal) end of the helical prothesis 40 and channel 42. An alternative anchor 60 and receptacle 62 is illustrated in FIG. 6B. It is preferred that the anchors be aligned in the plane of the stent surface. In this way, the anchor will not extend into the lumen of the blood vessel, potentially causing flow disturbance which in turn can be a source of thrombus formation.

Figure 7A:
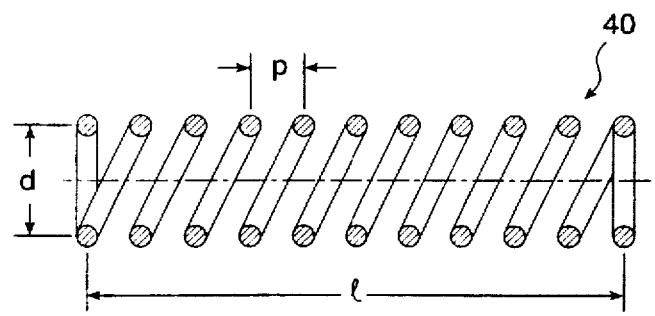
FIGS. 7A and 7B illustrate the expansion of a helical prosthesis from a constrained configuration (FIG. 7A) to an unconstrained configuration (FIG. 7B).
Figure 7B:
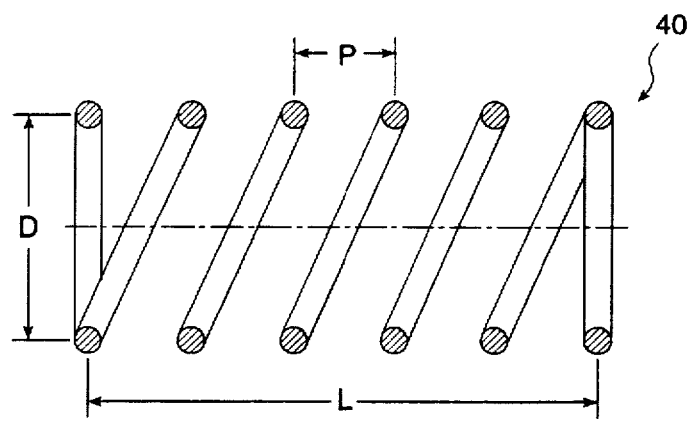

Referring now to FIGS. 7A and 7B, the helical prosthesis 40 will have a radially constrained configuration, as illustrated in FIG. 7A, and an unconstrained configuration, as shown in FIG. 7B. In the case of shape memory alloys, the unconstrained configuration 40 will exist at temperatures above the transition temperature, usually at slightly below body temperature in order to ensure that the prosthesis will fully deploy at body temperature. As shown in FIGS. 7A and 7B, the radially constrained prosthesis 40 in FIG. 7A has a length l which is equal to the length L of the expanded stent shown in FIG. 7B. The ability to maintain this length is achieved by increasing the number of helical turns in the constrained stent of FIG. 7A. Such a result must be intentionally achieved, since a reduction in diameter alone will generally result in a stent having an axially elongated configuration, i.e., winding down a coil formed from a fixed length of wire or ribbon while maintaining the same pitch between coils will result in axial elongation. In order to maintain the length, as the helical prosthesis 40 is reduced in diameter, it is necessary to increase the number of turns and reduce the spacing therebetween by the following formula:

$$p = P (d/D),$$

wherein p is the pitch or helical channel spacing on the catheter body, P is the pitch spacing between adjacent turns on the unconstrained prosthesis, d is the reduced diameter of the helical prosthesis, and D is the unconstrained diameter of the prosthesis.

In the exemplary embodiment illustrated herein, the pitch and the number of turns in the constrained stent is carefully controlled by forming the helical channel 42 according to the above formula. As can be seen, the rotatable barrel 30 of the stent will thus be configured to mate with a particular helical prosthesis 40. Conveniently, the catheters may be produced in kit form, where the rotatable barrel can be mated with a desired stent and cover. The stent and cover can be connected by the user to a suitable catheter body and other system components. Thus, the catheters may be separately packaged without a barrel. Barrels having different sizes may also be separately packaged, usually with the stent held on the barrel with the cover. The user may then use a desired barrel/stent combination with a "standard" catheter, reducing the need to inventory a catheter body for each stent size desired. The individual components will usually be in sterile packages, and a desired stent/barrel assembly can be mounted on the catheter body in the sterile operating field.

Figure 8:
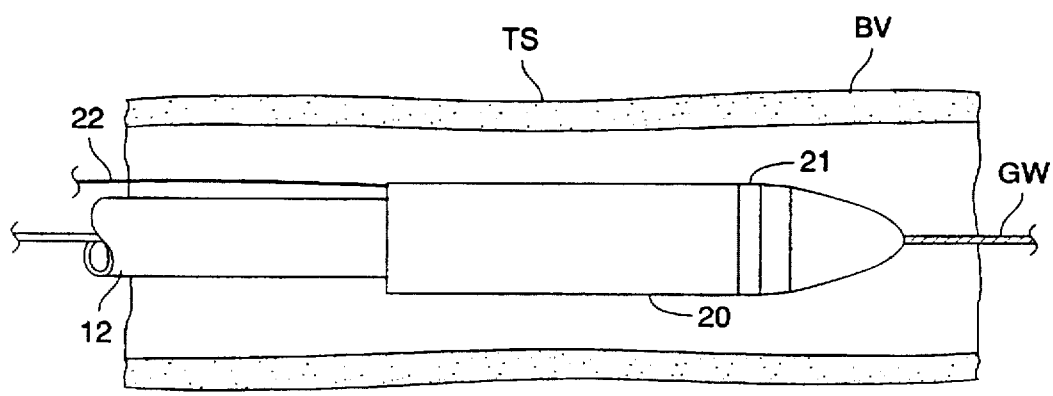
FIGS. 8–11 illustrate use of the catheter of FIG. 1 for delivering a helical prosthesis to a blood vessel.
Figure 9:
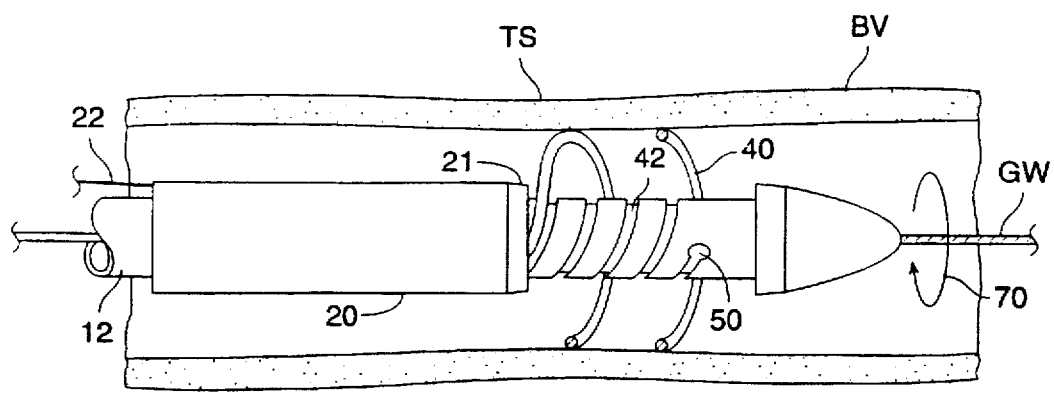
Figure 10:
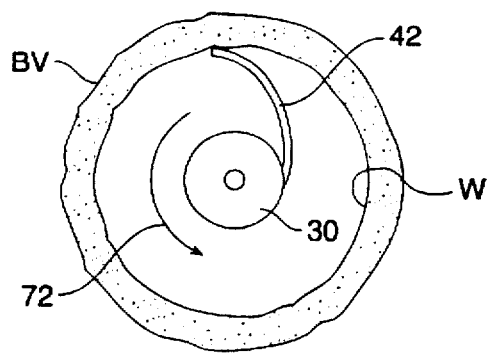
Figure 11:
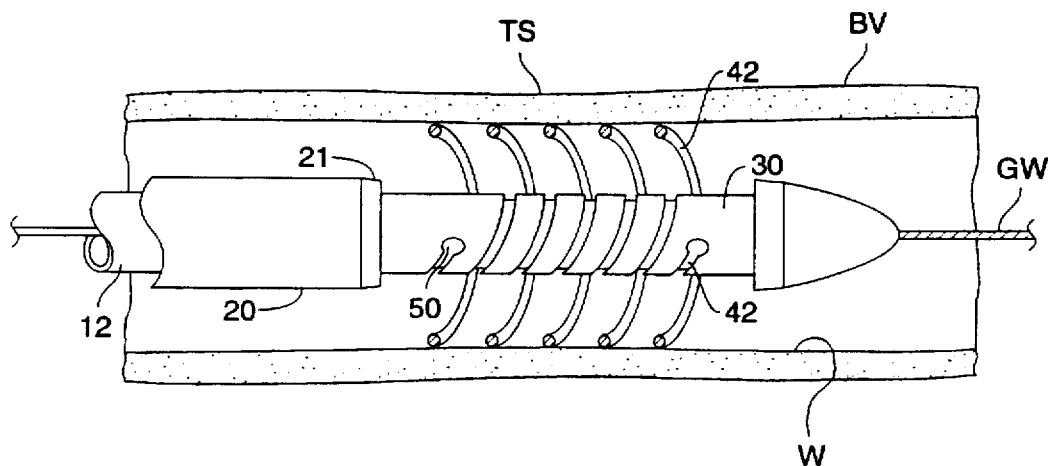

Use of the catheter system 10 for delivering the helical prosthesis 40 within a blood vessel BV is illustrated in FIGS. 8-11. The catheter 12 is delivered over a guidewire GW in a conventional manner to a target site TS within the blood vessel. As illustrated in FIG. 8, the retractable cover 20 remains fully covering the prosthesis. As the cover 20 is withdrawn, typically by the user drawing on the proximal end of pull wire 22 using the ring 24, the cover 20 retracts and releases the helical prosthesis 40 which engages the inner wall W of the blood vessel BV, as illustrated. As the cover continues to be retracted, the barrel rotates in the direction of arrow 70 in FIG. 9 and 72 in FIG. 10. After the cover 20 is fully retracted, as illustrated in FIG. 11, the prosthesis 42 is fully deployed.

Although the foregoing invention has been described in some detail by way of illustration and example, for purposes of clarity of understanding, it will be obvious that certain changes and modifications may be practiced within the scope of the appended claims.

What is claimed is:

1. A catheter carrying a self-expanding helical prosthesis, said catheter comprising:

a catheter body having a proximal end and a distal end;

a barrel rotatably attached to the distal end of the catheter body;

a self-expanding helical prosthesis disposed over the barrel; and an axially retractable cover disposed over said helical prosthesis, said cover maintaining the prosthesis in a radially reduced diameter condition;

wherein axial retraction of the cover allows the prosthesis to expand radially and wherein the barrel rotates as the prosthesis is deployed in a lumen which immobilizes a first released end of the stent.

2. A catheter as in claim 1, wherein the barrel has a helical channel formed thereover for receiving the helical prosthesis.

3. A catheter as in claim 2, wherein the helical channel has adjacent turns which are substantially equally spaced apart and wherein the spacing between turns conforms to the formula:

$$p = P (d/D),$$

wherein p is the helical channel spacing on the catheter body, P is the spacing between adjacent turns on the unconstrained prosthesis, d is the diameter of the helical prosthesis on the barrel, and D is the unconstrained diameter of the prosthesis.

4. A catheter as in claim 2, wherein the helical channel has a penetrable retaining structure formed thereover.

5. A catheter as in claim 4, wherein the retaining structure comprises a split membrane over the channel.

6. A catheter as in claim 5, wherein the split membrane is formed integrally with the catheter body.

7. A catheter as in claim 1, wherein the helical prosthesis has two ends and wherein at least one of those ends has an anchor formed thereon.

8. A catheter as in claim 7, wherein the helical channel has two ends and wherein at least one of those ends has a receptacle configured to mate with the anchor on the prosthesis.

9. A catheter as in claim 8, wherein the anchor is a flat loop or disk in the cylindrical plane of the prosthesis.

10. A catheter as in claim 1, further comprising a pull cord attached to a proximal end of the cover, wherein drawing on the pull cord axially retracts the cover.

11. A catheter as in claim 1, wherein the cover is a tubular sheath which continuously and uniformly covers the prosthesis.

12. A catheter as in claim 1, wherein the helical prosthesis when disposed on the barrel has a length in the range from 10 mm to 60 mm, an outer diameter in the range from 2 mm to 4 mm, and a number of turns in the range from 5 to 70.

13. A catheter as in claim 12, wherein the helical prosthesis when unconstrained has a length in the range from 10 mm to 60 mm an outer diameter in the range from 2.5 mm to 12 mm, and a number of turns in the range from 4 to 25.

14. A catheter for delivering self-expanding helical prostheses, said catheter comprising:

a catheter body having a proximal end, a distal end; and a helical channel formed near the distal end for receiving a helical prosthesis, wherein said channel has a penetrable retaining structure formed thereover; and an axially retractable cover over said helical channel, wherein said cover cooperates with the retaining structure to hold a helical prosthesis within the helical channel but when retracted allows the helical prosthesis to pass through the retaining structure.

15. A catheter as in claim 14, wherein the retaining structure comprises a split membrane over the channel.

16. A catheter as in claim 15, wherein the split membrane is formed integrally with the catheter body.

17. A catheter as in claim 14, wherein the catheter body comprises a rotatable barrel portion and wherein the helical channel is formed in said barrel portion, wherein axial retraction of the cover allows the prosthesis to expand radially and wherein the barrel rotates as the prosthesis is deployed in a lumen which immobilizes a first released end of the stent.

18. A catheter as in claim 14, wherein the helical channel has adjacent turns which are substantially equally spaced apart and wherein the spacing between turns conforms to the formula:

$$p=P \, (d/D),$$

wherein p is the helical channel spacing on the catheter body, P is the spacing between adjacent turns on the unconstrained prosthesis, d is the diameter of the helical prosthesis on the barrel, and D is the unconstrained diameter of the prosthesis.

19. A catheter as in claim 14, further comprising a helical prosthesis having two ends and wherein at least one of those ends has an anchor formed thereon.

20. A catheter as in claim 19, wherein the helical channel has two ends and wherein at least one of those ends has a receptacle configured to mate with the anchor on the prosthesis.

21. A catheter as in claim 19, wherein the anchor is a flat loop or disk in the cylindrical plane of the prosthesis.

22. A catheter as in claim 19, wherein the helical channel is configured to receive a prosthesis having a length in the range from 10 mm to 60 mm, an outer diameter in the range from 2 mm to 4 mm, and a number of turns in the range from 5 to 70.

23. A catheter as in claim 14, further comprising a pull cord attached to a proximal end of the cover, wherein drawing on the pull cord axially retracts the cover.

24. A catheter as in claim 23, wherein the cover is a tubular sheath which continuously and uniformly covers the prosthesis.

25. A catheter as in claim 24, wherein the helical prosthesis when unconstrained has a length in the range from 10 mm to 60 mm, an outer diameter in the range from 2.5 mm to 12 mm, and a number of turns in the range from 4 to 25.

26. A catheter system comprising a self-expanding helical prosthesis and a catheter for delivering said prosthesis, wherein the prosthesis comprises:

a helical prosthesis comprising a resiliently wound helical element having when unconstrained at body temperature a length, a diameter, and a number of turns;

wherein the catheter comprises:

a catheter body having a proximal end, a distal end, and a helical channel formed near the distal end thereof for receiving the prosthesis, wherein the helical channel has a number of turns and spacing between adjacent turns which allow the helical prosthesis to be carried in the channel in a radially reduced diameter condition with a length equal to the unconstrained length of the prosthesis.

27. A catheter system as in claim 26, wherein the helical channel has adjacent turns which are substantially equally spaced and wherein the spacing between turns conforms to the formula:

$$p=P \, (d/D),$$

wherein p is the helical channel spacing on the catheter body, P is the spacing between adjacent turns on the unconstrained prosthesis, d is the diameter of the helical groove, and D is the unconstrained diameter of the prosthesis.

28. A catheter system as in claim 26, wherein the catheter further comprises an axially retractable cover disposed over the helical channel, said cover holding the prosthesis in a radially reduced diameter condition.

29. A catheter as in claim 28, further comprising a pull cord attached to a proximal end of the cover, wherein drawing on the pull cord axially retracts the cover.

30. A catheter as in claim 29, wherein the cover is a tubular sheath which continuously and uniformly covers the prosthesis.

31. A catheter system as in claim 26, wherein the catheter body comprises a rotatable barrel portion and wherein the helical channel is formed in said barrel portion, wherein axial retraction of the cover allows the prosthesis to expand radially and wherein the barrel rotates as the prosthesis is deployed in a lumen which immobilizes a first released end of the stent.

32. A catheter as in claim 31, wherein the helical prosthesis when disposed on the barrel has a length in the range from 10 mm to 60 mm, an outer diameter in the range from 2 mm to 4 mm, and a number of turns in the range from 5 to 70.

33. A catheter as in claim 32, wherein the helical prosthesis when unconstrained has a length in the range from 10 mm to 60 mm, an outer diameter in the range from 2.5 mm to 12 mm, and a number of turns in the range from 4 to 25.

34. A catheter system as in claim 26, wherein the helical channel has a penetrable retaining structure formed thereover.

35. A catheter as in claim 34, wherein the retaining structure comprises a split membrane over the channel.

36. A catheter as in claim 35, wherein the split membrane is formed integrally with the catheter body.

37. A catheter as in claim 26, wherein the helical prosthesis has two ends and wherein at least one of those ends has an anchor formed thereon.

38. A catheter as in claim 37, wherein the helical channel has two ends and wherein at least one of those ends has a receptacle configured to mate with the anchor on the prosthesis.

39. A catheter as in claim 38, wherein the anchor is a flat loop or disk in the cylindrical plane of the prosthesis.

40. A method for loading a helical prosthesis on a catheter, said method comprising:

providing a self-expanding helical prosthesis having when unconstrained at body temperature a length, a diameter, and a number of turns; and radially constraining the prosthesis over the catheter, wherein the number of turns is increased relative to the unconstrained number in order to maintain the distance between the ends of the constrained prosthesis at a length equal to the unconstrained length of the prosthesis.

41. A method as in claim 40, wherein the prosthesis is constrained over the catheter so that the spacing between turns conforms to the formula $$p=P\ (d/D),$$

wherein p is the helical channel spacing on the catheter body, P is the spacing between adjacent turns on the unconstrained prosthesis, d is the diameter of the helical groove, and D is the unconstrained diameter of the prosthesis.

42. A method as in claim 40, wherein the constraining step comprises capturing the helical prosthesis within a cover which is axially retractably mounted on the catheter.

43. A method as in claim 40, wherein the constraining step comprises capturing the helical prosthesis within a helical channel on the catheter, wherein the channel has dimensions selected to hold the prosthesis with a length equal to its unconstrained length.

44. A method as in claim 43, wherein the helical prosthesis is constrained over the catheter to have a length in the range from 10 mm to 60 mm, an outer diameter in the range from 2 mm to 4 mm, and a number of turns in the range from 5 to 70.

45. A method for deploying a self-expanding helical stent, said method comprising:

providing a catheter having a self-expanding helical prosthesis rotatably mounted thereon, wherein said prosthesis is constrained in a radially collapsed configuration;

manipulating the catheter to position the prosthesis at a target site within a blood vessel;

progressively releasing successive turns of the helical prosthesis from one end thereof, wherein said one end first engages a wall of the blood vessel and thereafter the rotatably mounted portion of the prosthesis rotates as the prosthesis continues to be released.

46. A method as in claim 45, wherein said prosthesis is constrained on the catheter by a cover and wherein the successive turns of the prosthesis are released by retracting said cover.

47. A method as in claim 45, wherein the helical prosthesis has when unconstrained at body temperature a length, a diameter and a number of turns and wherein the number of turns when constrained on the catheter is increased so that the constrained catheter has a length equal to that of the unconstrained catheter.

48. A method as in claim 47, wherein the prosthesis is constrained within a helical channel on the catheter prior to release, and wherein the helical channel has adjacent turns which are substantially equally spaced apart and wherein the spacing between turns conforms to the formula:

$$p=P\ (d/D),$$

wherein p is the helical channel spacing on the catheter body, P is the spacing between adjacent turns on the unconstrained prosthesis, d is the diameter of the helical prosthesis, and D is the unconstrained diameter of the prosthesis.

49. A method as in claim 48, wherein the prosthesis is further constrained by a split membrane disposed over at least a portion of the helical channel, wherein the split membrane prevents direct contact between the prosthesis and the cover and permits release of the prosthesis after the cover has been retracted.

50. A kit comprising:

a rotatable barrel having a connector at one end and a helical channel, wherein the connector is rotatable mountable at the distal end of a catheter body;

a stent removably secured within the helical channel; and a package holding the barrel and stent.

51. A kit as in claim 50, further comprising a retractable cover over the stent on the barrel.

* * * * *